(12) United States Patent
Burisch et al.

(10) Patent No.: US 8,591,833 B2
(45) Date of Patent: Nov. 26, 2013

(54) TISSUE SAMPLE HANDLING APPARATUS

(75) Inventors: Arne Burisch, Braunschweig (DE);
Christian Löchte, Braunschweig (DE);
Annika Raatz, Braunschweig (DE);
Hermann Ulbrich, Bad Schoenborn (DE); Karl-Heinrich Westerhoff, Eppingen (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 0 days.

(21) Appl. No.: 13/451,584

(22) Filed: Apr. 20, 2012

(65) Prior Publication Data

US 2012/0271451 A1    Oct. 25, 2012

(30) Foreign Application Priority Data

Apr. 20, 2011   (DE) .......................... 10 2011 002 193

(51) Int. Cl.
*A61B 10/00*   (2006.01)

(52) U.S. Cl.
USPC ................. 422/536; 422/50; 422/63; 422/64; 422/65; 422/66; 436/180

(58) Field of Classification Search
USPC ................. 422/50, 536, 500, 63–67; 436/180
See application file for complete search history.

(56) References Cited

U.S. PATENT DOCUMENTS

| 5,821,115 | A | 10/1998 | Graupner | |
|---|---|---|---|---|
| 6,071,301 | A * | 6/2000 | Cragg et al. | 606/213 |
| 6,214,018 | B1 * | 4/2001 | Kreizman et al. | 606/130 |

FOREIGN PATENT DOCUMENTS

| DE | 20 2009 017 635 U1 | 7/2010 |
|---|---|---|
| JP | 2004333343 A | 11/2004 |
| JP | 2010060526 A | 3/2010 |
| WO | 0062035 A1 | 10/2000 |
| WO | 03039382 A2 | 5/2003 |

* cited by examiner

*Primary Examiner* — Jyoti Nagpaul
(74) *Attorney, Agent, or Firm* — Hodgson Russ LLP

(57) ABSTRACT

The invention relates to a tissue sample handling apparatus, in particular for grasping histological samples after infiltration of an embedding medium such as, for example, paraffin, which is characterized in that a sample is immobilizable on the handling apparatus, in particular in a sample holding position, by means of negative pressure.

20 Claims, 3 Drawing Sheets

TISSUE SAMPLE HANDLING APPARATUS

CROSS REFERENCE TO RELATED APPLICATIONS

Figure 1:
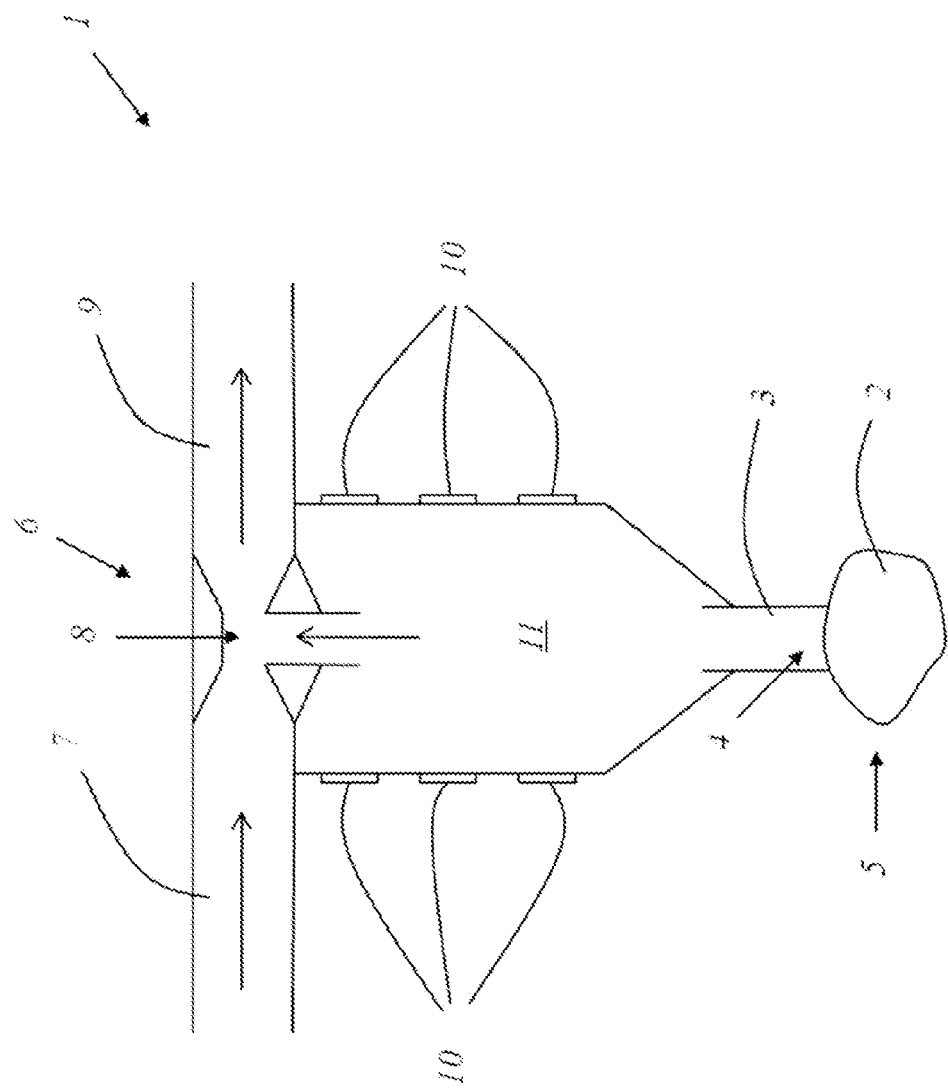

This application claims priority of German patent application number 10 2011 002 193.0 filed Apr. 20, 2011, the entire disclosure of which is incorporated by reference herein.

FIELD OF THE INVENTION

The invention relates to a tissue sample handling apparatus, in particular for grasping histological samples after infiltration of an embedding medium such as, for example, paraffin.

BACKGROUND OF THE INVENTION

When working with histological samples, in particular when preparing histological samples in the context of an embedding process for later microtoming, it is necessary to be able—in particular between individual process steps that as a rule occur at different laboratory locations and/or in different devices—to grasp the samples and set them down again precisely and gently. One of the difficulties existing in this context is that as a general rule the samples are impregnated or at least wetted with liquids, in particular with liquids that solidify at room temperature (for example, paraffin); this greatly complicates handling with the aid of mechanical grasping tools, for example tweezers. In addition, damage to the sample can occur.

Merely by way of example, mention is made below of a number of process steps during or between which it may be necessary to grasp samples and set them down again: In the context of the conditioning of histological samples, they are usually first fixed by the application of various chemicals. The tissue liquid originally present in the natural cavities of the sample is thereby replaced, in multiple steps, by a fixing liquid, for example by formalin. In order to convert the fixed samples into a state that permits sectioning by means of a microtome, the fixing liquid is replaced by an embedding medium, for example paraffin, gelatin, agar, nitrocellulose, polyester wax, polyethylene glycol, or plastic. During the aforementioned processes, the samples are usually located in a cassette that comprises a plurality of sieve-like openings so that the chemicals can flow around the samples. A particular embodiment of such a cassette is known, for example, from DE 43 33 118 A1. After infiltration of the embedding medium, i.e. for example paraffin, into the samples, the excess embedding medium is drained off. The samples can then be removed from the cassette. After this step, however, the samples can be located anywhere within the cassette; because of the paraffin residues adhering to them, for example, the samples as a rule adhere to the cassette cover, in the cassette cavity, and/or to one another. Stuck-together clumps of samples often form inside the cassette. This complicates reliable, gentle grasping of the individual samples.

Before further processing, in particular before automated, machine-controlled further processing, of the samples, for example before the further step of casting the samples into a paraffin block (called "blocking"), the sample or samples must be present in isolated fashion. Detachment and isolation can be performed, for example, using tweezers; disadvantageously, the risk exists that a sample may be damaged in this context and possibly even become unusable. In particular, the risk exists of unintentionally causing changes to a sample that result in artifacts upon later analysis of tissue sections of the sample.

DE 20 2009 017 635 U1 discloses a grasping apparatus for fixing specimens using a fixing agent. This grasping apparatus comprises a heatable and coolable probe. Also provided is a temperature regulation unit for heating and cooling the probe and for regulating the temperature of the probe in a range, the fixing agent exhibiting in that range a change in aggregate state from solid to liquid. Lastly, the paraffin adhering to a histological sample is used as an adhesion medium that, in the hardened (cooled) state, ensures that the sample to be grasped adheres to the probe. The sample can be detached again from the probe by subsequent heating of the probe, and thus re-liquefaction of the paraffin. In practice, this grasping apparatus is difficult to handle, especially because even liquefied paraffin still exerts an (albeit reduced) adhesive effect between the probe and sample. This, in particular, also disadvantageously prevents the use of this grasping apparatus in an automated system.

SUMMARY OF THE INVENTION

It is therefore the object of the present invention to describe a tissue sample handling apparatus that enables a sample to be efficiently, reliably, and gently grasped and released again.

The object is achieved by a tissue sample handling apparatus which is characterized in that a sample is immobilizable on the handling apparatus, in particular in a sample holding position, by means of negative pressure.

The invention has the very particular advantage that even samples that are wetted with a liquid, in particular with an embedding medium such as paraffin, can be grasped and set down again securely and gently, in particular without damage. Advantageously, the grasping and setting-down operations function sufficiently securely and reliably that according to the present invention automated handling of samples, in particular e.g. in the context of an automated sample processing procedure such as automated blocking, is also made possible with the tissue sample handling apparatus according to the present invention.

In a particularly advantageous embodiment of the tissue sample handling apparatus according to the present invention, a venturi nozzle is provided in order to generate the negative pressure. Provision can be made, in particular, that the venturi nozzle is operated with compressed air. An embodiment of this kind advantageously enables the generation of negative pressure with no possibility that movable components might become blocked by sucked-in liquids and/or solids, for example by sucked-in hardening paraffin. The venturi nozzle is instead very largely insensitive to sucked-in liquids or solids.

In an advantageous embodiment, a regulating apparatus is provided for regulating the negative pressure. For example, according to the present invention the negative pressure can be regulated, preferably automatically, as a function of whether or not a sample is immobilized on the handling apparatus, in particular in a sample holding position. In particular, provision can be made according to the present invention that the negative pressure is decreased, preferably automatically, when a sample is aspirated and immobilized on the handling apparatus, in order to reduce the forces acting on the sample and preferably limit them to the magnitude that is necessary in order to hold the sample on the handling apparatus, for example on an aspiration nozzle.

Alternatively or additionally, provision can advantageously be made that a greater negative pressure (lower pressure) is set when no sample is immobilized on the handling apparatus, for example in order to aspirate a sample securely and reliably. A reduction in negative pressure can occur, preferably once again automatically, after aspiration.

Especially in the interest of automated sample processing, in a particularly advantageous embodiment of the tissue sample handling apparatus according to the present invention a sensor apparatus is provided which determines whether or not a sample is immobilized on the handling apparatus, in particular in the sample holding position. For example, the sensor apparatus can comprise a pressure sensor that measures the respective current pressure in a chamber or conduit connected to the aspiration opening. With this embodiment, the determination is based on the fact that the pressure in the chamber or conduit drops immediately when the aspiration opening is entirely or partly closed off by the immobilized sample.

According to the present invention, the pressure sensor can in principle be arranged in all chambers or conduits, or also in a venturi nozzle, in which entire or partial closure of an aspiration opening by a sample has the effect of a change in pressure.

The tissue sample handling apparatus according to the present invention preferably comprises at least one aspiration nozzle. Provision can be made in particular that the location of the opening of the aspiration nozzle defines the sample holding position. The aspiration nozzle is preferably coordinated, in terms of the dimension of the aspiration opening, with the size of the samples to be immobilized. It is advantageous in particular if the aspiration nozzle offers the largest possible contact area for the sample, in order to distribute the force acting on the sample over the largest possible contact area.

On the other hand, the opening of the aspiration nozzle must not be selected to be so large that samples are unintentionally sucked in rather than being immobilized. For safety, however, according to the present invention a collector apparatus, for example having a collector sieve, can be provided, for example inside the tissue sample handling apparatus.

In an advantageous embodiment, provision is therefore made that the aspiration nozzle is exchangeable. An embodiment of the tissue sample handling apparatus in which different aspiration nozzles, in particular aspiration nozzles having a different opening diameter, are attachable and/or that comprises a storage apparatus, in particular a turret or slide magazine, for different aspiration nozzles, in particular aspiration nozzles having a different opening diameter, is particularly advantageous and particularly quickly adaptable to the respective utilization situation. For example, provision can be made that the respectively required aspiration nozzle can be brought into the working position, like the objectives of a microscope, by rotating an aspiration nozzle turret.

An advantageous embodiment of the tissue sample handling apparatus according to the present invention comprises a separation apparatus for separating a liquid and/or solids, in particular liquid paraffin, out of a gas stream, in particular an air stream, sucked in particularly through the aspiration nozzle. The separation apparatus can comprise an (in particular, cooled and/or coolable) condensation container. Alternatively or additionally, the separation apparatus can comprise an exchangeable condensation container and/or a condensation container that is embodied as a disposable container and/or single-use container. In the separation chamber, for example, the paraffin can be separated from a sucked-in paraffin mist.

In another embodiment, the separation apparatus contains a centrifugal separator.

In a very particularly advantageous embodiment, at least one heating apparatus is provided for heating at least a part of the tissue sample handling apparatus. This reliably prevents a liquid sucked in with a gas stream from solidifying unintentionally and/or at locations at which the solidified liquid, for example solidified paraffin, might result in a functional impairment.

In particular, provision can advantageously be made that at least one heating apparatus is provided for heating the aspiration nozzle or the multiple aspiration nozzles. Provision can also be made that at least one heating apparatus is provided for heating the venturi nozzle, and/or that at least one heating apparatus is provided for heating conduits, in particular tubing conduits.

The tissue sample handling apparatus according to the present invention may advantageously be embodied for (in particular, automatically) transporting a grasped sample into a predefined or predefinable set-down position. For this, the tissue sample handling apparatus can comprise, for example, a displacement apparatus, an X-Y-Z manipulator, or a robot arm that can move at least the aspiration nozzle in space, for example between a pickup position and a set-down position.

According to the present invention the tissue sample handling apparatus can also comprise an image processing system that, preferably automatically, detects a sample that is to be picked up and/or a set-down position for a sample to be set down. In particular, provision can furthermore be made that an open- or closed-loop control apparatus controls in open- and/or closed-loop fashion the position and/or the travel distance of the sample holding position and/or of the aspiration nozzle, and/or the negative pressure or optionally further parameters, in accordance with the information ascertained by the image processing system.

As already mentioned, the tissue sample handling apparatus according to the present invention can advantageously be part of an automatic handling machine or automatic sample preparation machine.

Further goals, advantages, features, and possible applications of the present invention are evident from the description below of an exemplifying embodiment with reference to the drawings. In this context, all features described and/or graphically depicted, independently or in any useful combination, constitute the subject matter of the present invention, irrespective of their grouping in the claims or their internal references.

BRIEF DESCRIPTION OF THE DRAWING VIEWS

Figure 2:
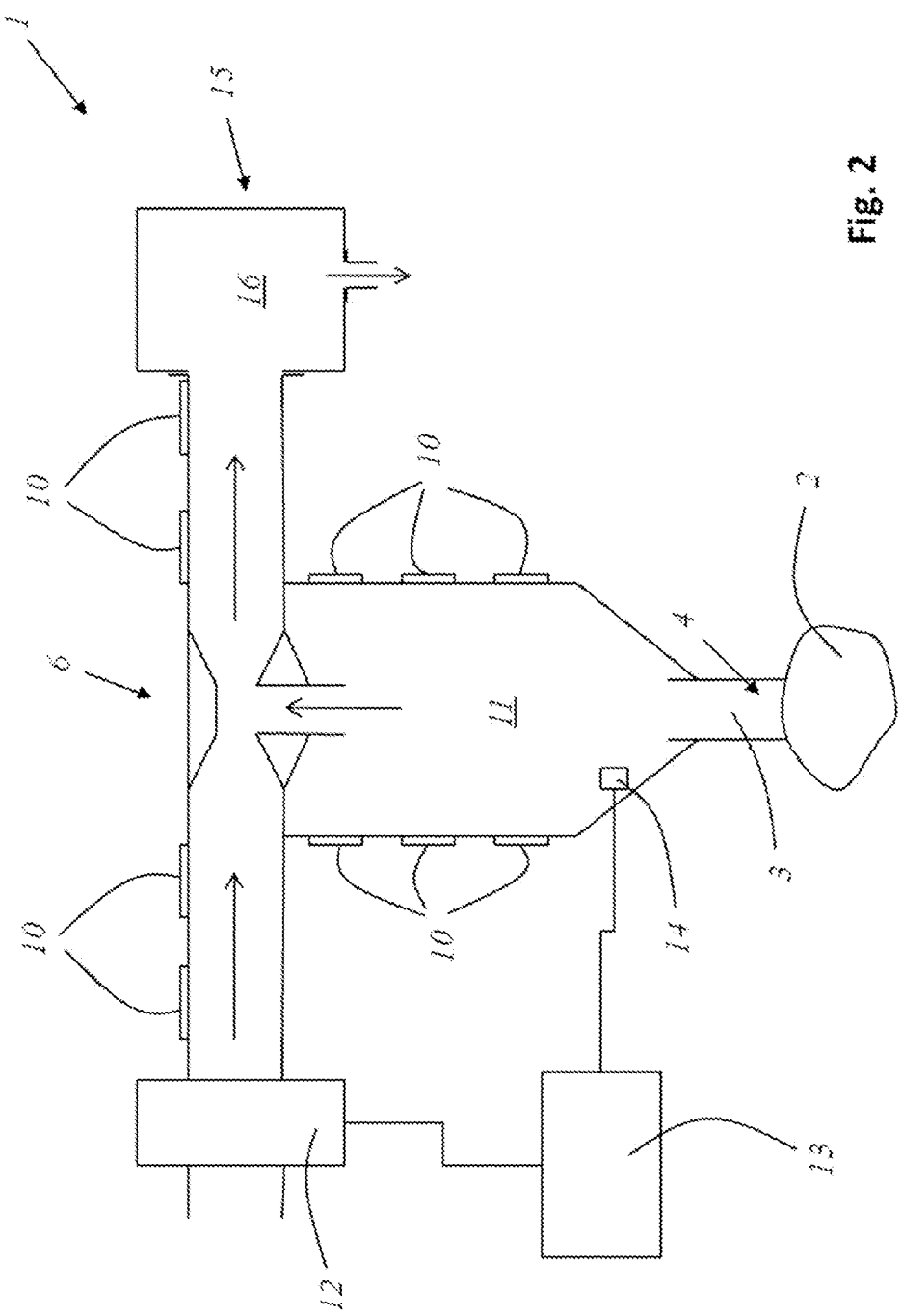
Figure 3:
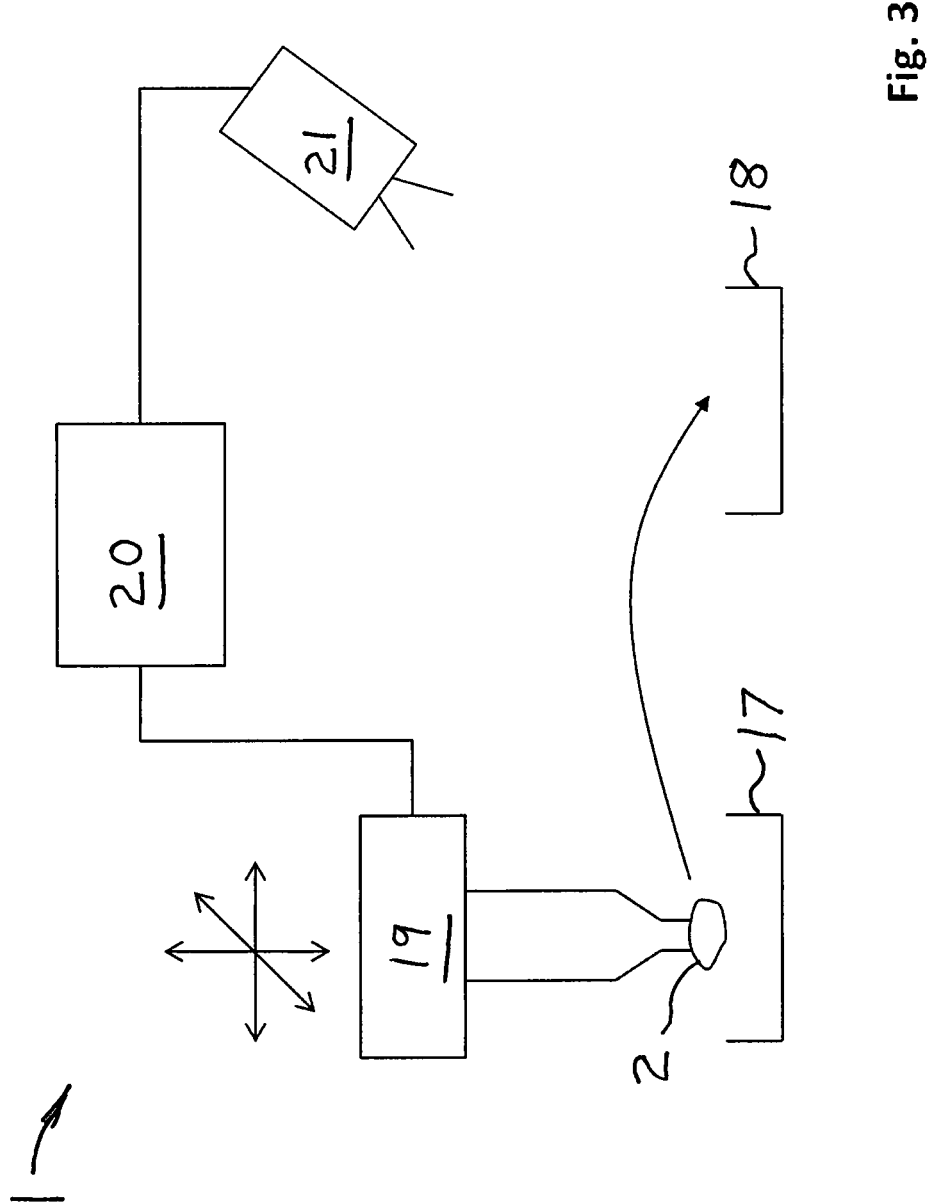

In the drawings:

FIG. 1 schematically shows a tissue sample handling apparatus according to the present invention;

FIG. 2 shows a further tissue sample handling apparatus according to the present invention having a negative-pressure control system and a separation apparatus; and FIG. 3 shows an automatically operating tissue sample handling apparatus according to the present invention.

DETAILED DESCRIPTION OF THE INVENTION

FIG. 1 schematically shows a tissue sample handling apparatus 1 according to the present invention for grasping a histological sample 2 and setting it down again.

Tissue sample handling apparatus 1 comprises an aspiration nozzle 3 whose aspiration opening 4 defines a sample holding position 5. Sample 2 can be immobilized in sample holding position 5 by means of negative pressure.

To generate the negative pressure, tissue sample handling apparatus 1 comprises a venturi nozzle 6 that is operated with compressed air. Compressed air is delivered via a compressed-air conduit 7, flows through a constriction 8, and then flows, together with the air (which if applicable may contain a paraffin mist) sucked through aspiration opening 4, through an exhaust air conduit 9.

Located between aspiration nozzle 3 and venturi nozzle 6 is an aspiration chamber 11 that is heatable with the aid of heating apparatuses 10.

FIG. 2 shows a further tissue sample handling apparatus 1 according to the present invention that, in terms of basic function, operates exactly like tissue sample handling apparatus 1 depicted in FIG. 1. An open- and closed-loop control apparatus 13 that controls, by means of a valve 12, the pressure of the compressed air delivered to venturi nozzle 6 as a function of the negative pressure in aspiration chamber 11, is additionally provided. The negative pressure in aspiration chamber 11 is measured with the aid of a pressure sensor 14 that forwards measurement signals to open- and closed-loop control apparatus 13.

Because the pressure in aspiration chamber 11 drops immediately when aspiration opening 4 is closed off entirely or partly by the immobilized sample, open- and closed-loop control apparatus 13 can ascertain, with the aid of pressure sensor 14, whether or not a sample is immobilized in sample holding position 5.

In addition, when a sample 2 is immobilized in sample holding position 5, open- and closed-loop control apparatus 13 lowers the negative pressure in aspiration chamber 11, by reducing the pressure of the compressed air, to a magnitude that is sufficient to hold sample 2 in sample holding position 5. This limits the forces acting on the sample, in a manner that is gentle on the sample, to the requisite magnitude.

Tissue sample handling apparatus 1 comprises a separation apparatus 15, namely a cooled and exchangeable condensation container 16. Condensation container 16 is embodied as a disposable, single-use container. In condensation container 16, for example, paraffin can be separated from a paraffin mist that has been sucked in.

Further heating apparatuses 10 for heating compressed-air conduit 7, venturi nozzle 6, and exhaust air conduit 9 are additionally provided.

FIG. 3 shows an automatically operating tissue sample handling apparatus 1 according to the present invention that is embodied for autonomously and automatically grasping a sample 2, for example out of a cassette 17, and setting it down again at another location, for example in an embedding mold 18.

Tissue sample handling apparatus 1 comprises an X-Y-Z manipulator 19 that can move at least aspiration nozzle 3 together with aspiration chamber 11 freely in space, under the control of a central control system 20.

Central control system 20 controls X-Y-Z manipulator 19 as a function of the information transmitted to it from an image processing system 21 that automatically detects a sample 2 that is to be picked up, and the respective set-down position for a sample 2 that is to be set down.

PARTS LIST

1 Tissue sample handling apparatus
2 Sample
3 Aspiration nozzle
4 Aspiration opening
5 Sample holding position
6 Venturi nozzle
7 Compressed-air conduit
8 Constriction
9 Exhaust air conduit
10 Heating apparatuses
11 Aspiration chamber
12 Valve
13 Open- and closed-loop control apparatus
14 Pressure sensor
15 Separation apparatus
16 Condensation container
17 Cassette
18 Embedding mold
19 X-Y-Z manipulator
20 Central control system
21 Image processing system

What is claimed is:

1. A tissue sample handling apparatus (1) for grasping histological samples (2) after infiltration of an embedding medium, the tissue sample handling apparatus comprising:
   a conduit (7) delivering a flow of compressed air;
   a sample holding position (5) spaced from the flow of compressed air; and
   a venturi nozzle (6) arranged downstream from the conduit (7) for receiving the flow of compressed air from the conduit (7), the venturi nozzle (6) having a constriction (8) through which the flow of compressed air passes, wherein the venturi nozzle (6) generates a negative pressure at the sample holding position (5);
   wherein a sample (2) is immobilizable on the handling apparatus (1) in the sample holding position (5) by means of the negative pressure generated by the venturi nozzle.

2. The tissue sample handling apparatus (1) according to claim 1, further comprising a regulating apparatus (13) for regulating the negative pressure.

3. The tissue sample handling apparatus (1) according to claim 1, further comprising a sensor apparatus providing a signal indicating whether or not a sample (2) is immobilized on the handling apparatus (1) in the sample holding position (5).

4. The tissue sample handling apparatus (1) according to claim 3, further comprising a chamber (11) between the venturi nozzle (6) and the sample holding position (5), wherein the sensor apparatus comprises a pressure sensor (14) arranged to measure pressure in the chamber (11).

5. The tissue sample handling apparatus (1) according to claim 3, wherein the sensor apparatus comprises a pressure sensor (14) arranged to measure pressure in the conduit (7).

6. The tissue sample handling apparatus (1) according to claim 1, further comprising at least one aspiration nozzle (3) in communication with venturi nozzle (6).

7. The tissue sample handling apparatus (1) according to claim 6, wherein the aspiration nozzle (3) has an opening diameter and is exchangeable with at least one different aspiration nozzle (3) having a different opening diameter.

8. The tissue sample handling apparatus (1) according to claim 7, further comprising a storage apparatus for storing a plurality of aspiration nozzles (3) each having a different opening diameter.

9. An automatic handling machine or automatic sample preparation machine having a tissue sample handling apparatus (1) according to claim 8.

10. The tissue sample handling apparatus (1) according to one of claim 6, further comprising a separation apparatus (15) for separating a liquid and/or solid objects out of an air stream sucked in through the aspiration nozzle (3).

11. The tissue sample handling apparatus (1) according to claim 10, wherein the separation apparatus (15) comprises a condensation container (16).

12. The tissue sample handling apparatus (1) according to claim 11, wherein the condensation container (16) is exchangeable with a replacement condensation container (16).

13. The tissue sample handling apparatus (1) according to claim 12, wherein the condensation container (16) is a disposable container.

14. The tissue sample handling apparatus (1) according to claim 12, wherein the condensation container (16) is a single-use container.

15. The tissue sample handling apparatus (1) according to claim 11, wherein the condensation container (16) is a cooled or coolable.

16. The tissue sample handling apparatus (1) according to claim 6, further comprising at least one heating apparatus (10) for heating at least a part of the tissue sample handling apparatus (1).

17. The tissue sample handling apparatus (1) according to claim 16, wherein the apparatus (1) includes a chamber (11) connecting the aspiration nozzle (3) with the venturi nozzle (6), and wherein the at least one heating apparatus (10) is operable to heat at least one of the following: the venturi nozzle (6), the aspiration nozzle (3), the chamber (11), and the conduit (7).

18. The tissue sample handling apparatus (1) according to claim 1, further comprising an X-Y-Z manipulator (19) for transporting a grasped sample (2) into a predefined or predefinable set-down position.

19. The tissue sample handling apparatus (1) according to claim 18, further comprising an image processing system (18) that detects a sample (2) that is to be picked up and/or a set-down position for a sample (2) to be set down.

20. The tissue sample handling apparatus (1) according to claim 19, further comprising an open- or closed-loop control apparatus (20) that controls in open- and/or closed-loop fashion at least one of the following in accordance with the information ascertained by the image processing system (21): the sample holding position, a travel distance of the sample holding position, a position of the aspiration nozzle (3), a travel distance of the aspiration nozzle (3), and the negative pressure.

* * * * *